United States Patent
Lundstedt

(10) Patent No.: US 6,855,327 B1
(45) Date of Patent: Feb. 15, 2005

(54) PESTICIDE DISPERSANT

(75) Inventor: Alan P. Lundstedt, Cincinnati, OH (US)

(73) Assignee: Cognis Corporation, Cincinnati, OH (US)

( * ) Notice: Subject to any disclaimer, the term of this patent is extended or adjusted under 35 U.S.C. 154(b) by 495 days.

(21) Appl. No.: 09/334,366

(22) Filed: Jun. 16, 1999

Related U.S. Application Data

(60) Provisional application No. 60/091,635, filed on Jul. 2, 1998.

(51) Int. Cl.$^7$ .................. A01N 25/00; A01N 25/08; A01N 43/04; A61K 31/715; A61K 47/00

(52) U.S. Cl. .................. 424/405; 424/409; 514/54; 514/788; 514/943; 514/975; 504/116.1

(58) Field of Search .................. 504/116, 116.1; 424/405, 409; 514/788, 943, 975, 23, 54

(56) References Cited

U.S. PATENT DOCUMENTS

| | | | |
|---|---|---|---|
| 3,920,442 A | 11/1975 | Albert et al. .................. 71/92 | |
| 3,986,979 A | 10/1976 | Moorer et al. .............. 252/353 | |
| 4,472,170 A | 9/1984 | Hellyer | |
| 4,597,770 A | 7/1986 | Forand et al. | |
| 4,895,622 A | 1/1990 | Barnett et al. | |
| 4,936,901 A | 6/1990 | Surgant, Sr. et al. ........... 71/92 | |
| 5,266,690 A | 11/1993 | McCurry, Jr. et al. ..... 536/18.6 | |
| 5,385,750 A | 1/1995 | Aleksejczyk et al. .......... 427/4 | |
| 5,449,763 A | 9/1995 | Wulff et al. ................ 536/18.6 | |
| 5,500,219 A | 3/1996 | Utz et al. .................... 424/409 | |
| 5,550,115 A | 8/1996 | Garst et al. .................... 514/25 | |
| 5,559,078 A | * 9/1996 | Garst ......................... 504/116 | |
| 5,622,658 A | 4/1997 | Lloyd et al. .................. 264/15 | |
| 5,639,465 A | 6/1997 | Huang et al. ............... 424/409 | |
| 5,714,439 A | 2/1998 | Houghton et al. .......... 504/339 | |
| 5,883,112 A | * 3/1999 | Pilato et al. ................. 514/404 | |
| 6,015,910 A | * 1/2000 | Wu ........................ 548/367.7 | |

FOREIGN PATENT DOCUMENTS

| | | |
|---|---|---|
| EP | 0 498 145 | 8/1992 |
| EP | 0 922 388 | 6/1999 |
| GB | 2 311 939 | 10/1997 |
| WO | 98/33383 | 8/1998 |
| WO | WO 98/33383 | 8/1998 |

* cited by examiner

*Primary Examiner*—Sreeni Padmanabhan
*Assistant Examiner*—Lauren Q. Wells
(74) *Attorney, Agent, or Firm*—Aaron R. Ettelman; Steven J. Trzaska; Daniel S. Ortiz

(57) ABSTRACT

Free-flowing granular dispersing agents for use in water-dispersible granule (WDG) agricultural chemical formulations are a composite substance comprised of an alkyl polyglycoside and a polymeric anionic dispersant. The granular composite dispersing agents can be used in granular or liquid agricultural chemical formulations, exhibit outstanding attrition resistance, excellent dispersional stability after accelerated aging and low moisture content when made into a paste. The composite dispersing agents are useful as primary dispersants in dry agricultural formulations (wettable powders and water-dispersible granules) and in aqueous suspension concentrates.

20 Claims, No Drawings

PESTICIDE DISPERSANT

CROSS-REFERENCE TO RELATED APPLICATIONS

This application claims the benefit of copending provisional application Ser. No. 60/091,635, filed on Jul. 2, 1998, the entire contents of which are incorporated herein by reference.

STATEMENT REGARDING FEDERALLY SPONSORED RESEARCH OR DEVELOPMENT

Not Applicable.

BACKGROUND OF THE INVENTION

Water-dispersible granule (abbreviated WDG) pesticide formulations are known. These formulations are desirable because they avoid the use of potentially toxic solvents and permit the use of easily-disposable paper containers or water, soluble containers. In addition, such formulations are less dusty than wettable powder formulations. As a result, potential exposure of pesticide applicators and the general public to the pesticide or solvent is thereby reduced. Dispersible granular pesticide formulations are typically prepared by blending premilled, water-insoluble, active ingredient, dispersing agents, disintegrating agent and wetting agents in an aqueous suspension. The aqueous mix is extruded to form granules which are then dried to yield the final product.

A dispersible granule herbicide composition designed for dispersion in a liquid carrier should ideally have a high content of active material, should be resistant to mechanical breakdown into a dust (attrition) should be readily dispersible in the carrier and should then form a dispersion which is as stable as possible, requiring a minimum of subsequent agitation to maintain homogeneity.

It would be desirable to produce a product with higher attrition resistance and correspondingly less dust formation resulting from normal handling including bagging, shipping and loading and provide good dispersional stability in spray solutions. Such a product would have improved qualities in terms of less worker exposure hazard to the pesticide due to the formation of smaller amounts of dust.

BRIEF SUMMARY OF THE INVENTION

In its broadest aspect, the present invention relates to liquid or granular dispersing agents for use in water-dispersible granule (WDG) or suspension concentrate agricultural chemical formulations which are composite substances comprised of an alkyl polyglycoside and a polymeric anionic dispersant. The granular composite dispersing agents are made by drying together aqueous mixtures of alkyl polyglycosides and dispersing agents to form a dry, powdered product providing significant advantages over conventional wetting and dispersing agents added individually to pesticide formulations. The granular composite dispersing agents according to the invention, which can be used in granular or liquid-suspension agricultural chemical formulations, exhibit outstanding attrition resistance, excellent dispersional stability after accelerated aging and low moisture content when made into a paste. The composite dispersing agents are useful as primary dispersants in dry agricultural formulations (wettable powders and water-dispersible granules) and in aqueous suspension concentrates.

Another aspect of the present invention relates to liquid composites which are comprised of an alkyl polyglycoside and a polymeric anionic dispersant.

BRIEF DESCRIPTION OF THE SEVERAL VIEWS OF THE DRAWING

Not Applicable.

DETAILED DESCRIPTION OF THE INVENTION

As used herein, the abbreviation APS stands for alkyl polysaccharide which is a generic term for an alkyl polyglycoside.

The polymeric anionic dispersant that can be used in this invention is any polymeric dispersant material having multiple anionic groups and which is capable of forming a composite with an alkyl polyglycoside. Such polymeric anionic substances include, but are not limited to, sulfonated lignins, sulfonated naphthalene-formaldehyde condensates, and sulfonated polystyrenes. These compounds are described in U.S. Pat. No. 4,936,901, the entire contents of which are incorporated herein by reference.

Sulfonated lignins, which are also referred to as lignosulfonates, are described in U.S. Pat. No. 3,986,979, the entire contents of which are incorporated herein by reference. One of the main sources of lignins is the paper and pulp industry where lignocellulosic materials such as wood, straw, corn stalks, bagasse, and the like are processed to separate the cellulose or pulp from the lignin. When lignin is obtained from the kraft or sulfate pulping processes, it must be sulfonated before use as a dispersing agent. For example, the lignin products obtained in an alkaline or neutral process of digestion of lignocellulosic materials may be readily sulfonated by reacting with a bisulfite or sulfite. In other pulping processes, such as the sulfite process, lignin is made soluble by sulfonation and thus separated from the cellulose by dissolving in the spent liquor and is present in this liquor as a lignosulfonate. Any of the above-described sulfonated lignin materials may be used to produce the dispersing agent of the present invention. The degree of refining to which these sulfonated lignin materials are subjected, will depend on the quality of product desired and upon the economic factors involved. That is, refining to some extent will improve the properties of the final processed product, but the degree of improvement will not always be economically justifiable.

Although sulfonated lignins from all sources are contemplated, the sulfonated lignins made from alkali lignin are preferred. Particularly preferred are the alkali metal salts of alkali lignin, particularly sodium sulfonated lignin. Although sodium sulfonated lignin is preferred, chemically modified sulfonated lignins may be used. These lignins are commercially available from, for example, Westvaco under the trademark names REAX®, POLYFON®, and KRAFTSPERSE®, or from Lignotech USA under the trademark names BORRESPERSE®, ULTRAZINE®, UFOXANE®, MARASPERSE®, and DIWATEX®, or from Witco under the trademark name MORWET® D425.

The sulfonated naphthalene-formaldehyde condensates are described in U.S. Pat. No. 4,936,901, column 16, line 67 to column 17, line 21. The sulfonated polystyrenes are described in U.S. Pat. No. 4,936,901, column 17, lines 2240.

The dry powder or granular composite compositions according to the invention can be made by mixing the components in solution together and drying. Typically, the process for making the composites comprises mixing aqueous polymeric anionic dispersants and alkyl polyglycosides together at a temperature of from about 165° F. to about 185° F. primarily to adjust viscosity control of the feedstock to maximize the uniformity of the spray pattern. The mixture is then typically allowed to stand for a time sufficient to assure complete dissolution of the alkyl polyglycoside in the solution. Any number of conventional drying methods may be used. For instance, spray drying, force air drying, oven drying, drum drying, and freeze drying, with spray drying being preferred. Spray drying is preferred and the parameters necessary are well known to those skilled in the art, however, particularly successful products may be spray dried at air inlet temperatures of from 200° to 900° F. and outlet air temperatures of between 1550 and 400° F. The aqueous mixture of wetting and dispersing agent is normally diluted and/or heated to an easily handled viscosity prior to spray drying, i.e., 30–45% solids content.

The ratio of alkyl polyglycoside to the polymeric anionic dispersant can be any ratio required and is dependent upon the particular pesticide contemplated and whether the composite will be in the dry powder form or the liquid form. Preferably, the weight ratio (on a dry solids basis) of alkyl polyglycoside to polymeric anionic dispersant can be from about 1:9 to about 9:11 and is most preferably from about 1:4 to about 7:13 in the case of the dry powder form. This corresponds to a weight percentage of alkyl polyglycoside of from about 10% to about 45% in the preferred embodiment and from about 20% to about 35% in the most preferred embodiment. A particularly preferred composition is comprised of an alkyl polyglycoside and a sulfonated lignin in a weight ratio of alkyl polyglycoside to sulfonated lignin of about 1:3. Preferably, the upper limit of 45% by weight of alkyl polyglycoside is used in making dry powder composites according to the invention wherein the polymeric anionic dispersant is sulfonated lignin. Greater amounts of alkyl polyglycoside can interfere in the efficient manufacture of such dry powder composites in the drying operations, particularly in spray drying. For liquid composites, any ratio of alkyl polyglycoside to the water-soluble sulfonated lignin can be used as desired and is dependent upon the particular pesticide contemplated. For liquid composites, the amount of alkyl polyglycoside may exceed 45% by weight of the composite.

The alkyl polyglycosides which can be used in the invention have the formula I

$$R_1O(R_2O)_b(Z)_n \qquad\qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions according to the invention have the formula I wherein Z is a glucose residue and b is zero. Such alkyl polyglycosides are commercially available, for example, as APG®, GLUCOPON®, PLANTAREN® or AGRIMUL® surfactants from Henkel Corporation, Ambler, Pa., 19002. Examples of such surfactants include but are not limited to:

1. GLUCOPON® 220 Surfactant—an alkyl polyglycoside in which the alkyl group contains 8 to 10 carbon atoms and having an average degree of polymerization of 1.5.
2. GLUCOPON® 225 Surfactant—an alkyl polyglycoside in which the alkyl group contains 8 to 10 carbon atoms and having an average degree of polymerization of 1.7.
3. GLUCOPON® 600 Surfactant—an alkyl polyglycoside in which the alkyl group contains 12 to 16 carbon atoms and having an average degree of polymerization of 1.4.
4. GLUCOPON® 625 Surfactant—an alkyl polyglycoside in which the alkyl group contains 12 to 16 carbon atoms and having an average degree of polymerization of 1.4.
5. APGO 325 Surfactant—an alkyl polyglycoside in which the alkyl group contains 9 to 11 carbon atoms and having an average degree of polymerization of 1.6.
6. PLANTAREN® 2000 Surfactant—an alkyl polyglycoside in which the alkyl group contains 8 to 16 carbon atoms and having an average degree of polymerization of 1.4.
7. PLANTAREN® 1300 Surfactant—an alkyl polyglycoside in which the alkyl group contains 12 to 16 carbon atoms and having an average degree of polymerization of 1.6.
8. AGRIMUL® PG 2067 Surfactant—an alkyl polyglycoside in which the alkyl group contains 8 to 10 carbon atoms and having an average degree of polymerization of 1.7.
9. AGRIMUL® PG 2076 Surfactant—an alkyl polyglycoside in which the alkyl group contains 8 to 10 carbon atoms and having an average degree of polymerization of 1.5.

Other examples include alkyl polyglycoside surfactant compositions which are comprised of mixtures of compounds of formula I as described in U.S. Pat. Nos. 5,266,690 and 5,449,763, the entire contents of both of which are incorporated herein by reference.

Extruded WDGs can be prepared on a Benchtop Granulator by Luwa using a 0.8 mm screen and setting the motor speed to about mid-scale, with small adjustments made to compensate for variations in paste rheology, using slower speeds for thicker pastes. Pan-granulated WDGs can be prepared using a 15-inch diameter rotating pan. The precise conditions required to produce the granules by either method can be determined for each combination of pesticide, dispersant, and other formulation components to minimize the proportion of oversize and undersize material. This can be done readily by one skilled in the art by visual observation of granule sizes.

The composites according to the invention, both granular and liquid, can be used in any type of agricultural formulation examples of which include, but are not limited to, those containing such biologically active substances as insecticides, nematocides, fungicides, miticides, herbicides, and growth regulators such as those described in U.S. Pat. No. 5,559,078. The composites according to the invention are used as a dispersant in a pesticide formulation in an amount effective to emulsify the biologically active ingredient. Typically, the weight percentage (on a dry solids basis) of the composites according to the invention in pesticide formulations can be from about 2% to about 99% and is preferably from about 4% to about 16%. The formulations can contain other surfactants including nonionics, anionics, cationics, amphoterics and combinations thereof as well as inert fillers and the like.

When used in WDG formulations, the composites according to the invention impart superior attrition resistance while achieving good disintegration rates, maintain excellent dispersional stability after accelerated aging, allow the production of granules with higher bulk densities, which promotes free flow of the final granulated products and, in many cases, reduces the moisture content in extrusion paste. Formulations prepared with the dry composite dispersant system typically show enhanced performance when compared with otherwise equivalent formulations made by adding the alkyl polyglycoside and polymeric anionic dispersants as separate components. The dry powder form of the composite according to the invention provides a water-free surfactant that facilitates dry blending and grinding to make wettable powders and WDG premixes. The liquid dispersant form of the composite according to the invention can be added to WDG premixes or liquid formulations containing insoluble suspended solids (including formulation types known as aqueous flowables, suspension concentrates, or suspoemulsions).

The following examples are meant to illustrate but not to limit the invention.

EXAMPLE 1

A blend was prepared by mixing 300 g AGRIMUL® PG 2069 (as a liquid containing 50% solids in water) at 40° C. with 700 g REAX® 100M (as a liquid containing 40% water) at 40° C. and stirring manually for 2 minutes to attain a homogeneous mixture. Over the next 3 days, the mixture was left undisturbed and was allowed to equilibrate to ambient temperature. During this time, the mixture remained homogeneous and did not show evidence of any chemical reaction or physical separation. The blend was spray-dried according to the conditions set forth in Example 1 of U.S. Pat. No. 3,986,979. The resulting solid was a free-flowing powder that dissolved completely in water at 18° C.

EXAMPLE 2

A blend was prepared by adding 7.8 Kg AGRIMUL® PG 2076 (as a liquid containing 60% solids in water) at 35° C. with 42.2 Kg REAX® 85A (as a liquid containing 26% solids in water) at 35° C. and stirring manually for 2 minutes to attain a homogeneous mixture. Sufficient concentrated sulfuric acid was then added while stirring so as to adjust the pH to 8.5 and the mixture was allowed to equilibrate to ambient temperature for 2 days. The liquid mixture was spray dried to yield a free flowing powder that dissolved completely in water at 21° C.

EXAMPLE 3

The procedure of Example 2 was repeated except that 11.1 Kg AGRIMUL® PG 2069 and 38.9 Kg REAX® 88B were used. This mixture was acidified to pH 8.5 by adding sulfuric acid. The spray-dried solid was observed to flow freely and dissolved completely in water at 21° C.

EXAMPLE 4

A set of wettable powders were prepared according to the following procedure to evaluate the effect of different dispersants (a–d) in a prototypical formulation. For each formulation, the four components were pre-blended manually and then the pre-blend was passed through a 4-inch air mill to produce a wettable powder.

| Wt % | Component |
|---|---|
| 84.2% | Chlorothalonil (95%) |
| 8.0% | Dispersant (see table below) |
| 1.0% | SELLOGEN ® W |
| 6.8% | ATTACOTE ® LVM |

SELLOGEN ® W is a trademark product of Henkel Corporation and is an alkyl naphthalene sulfonate.
ATTACOTE ® LVM is a trademark product of Engelhard Corporation and is an attapulgite clay.
Chlorothalonil (tetrachloroisophthalonitrile) is manufactured by several companies and is sold, for example, as a 95–97% technical grade fungicide under the trade name DACONIL ® by ISK Biosciences.

The following dispersants were used in the above formulation.

| Formulation | Dispersant |
|---|---|
| a | REAX ® 85A (as a 100% solid) |
| b | solid from example 2 |
| c | REAX ® 88B (as a 100% solid) |
| d | solid from example 3 |

The wetting time was evaluated for each wettable powder as follows. 5.0 grams of powder was quickly placed onto the surface of 100 mL of water (containing 500 ppm hardness) in a 250 mL beaker, distributing the powder over the surface as quickly and evenly as possible. A stop watch was used to measure the time required to completely wet the powder. Formulation Wetting time (seconds)

| Formulation | Wetting time (seconds) |
|---|---|
| a | 3420 |
| b | 86 |
| c | 1500 |
| d | 57 |

EXAMPLE 5

The following procedure was used to measure attrition of the WDGs described herein. To a 100 mL round glass bottle was added 5 grams of WDG and 20 grams of 5-mm high-density alumina shot. The bottle was rotated on a Turbulator blender (Glen Mills Inc., Clifton, N.J.) for 2 minutes. The attrition is computed as the weight percent of the mechanical breakdown of the granules that passed through a U.S. Standard sieve with 400-micron apertures.

EXAMPLE 6

Wettable powders were made as described in Example 4 except the dispersant was used at 12%, SELLOGEN® W was used at 3%, and 1% sodium sulfate was used in place of ATTACOTE® LVM. The wettable powders were converted into extruded WDGs by (1) spraying a fine mist of water onto the powder contained in a round quart jar while rotating the jar manually until the powder was transformed into a uniformly wet paste, (2) extruding the paste through a 0.8 mm screen to yield extruded granules that were typically 2–4 mm in length, and (3) drying the extrudate in a fluid bed dryer for about one hour at 45° C., which yielded granules containing 1–2% moisture. The dispersibility was measured by the number of complete inversions required to completely disperse 1.25 g of test material in 250 mL of water of standard hardness contained in a 250 mL graduated cylinder. The suspensibility was measured according to CIPAC MT 15.1 in water of standard hardness at 25+/−1° C. The term "paste" refers to the extrudable wet mixture that is obtained by spraying water onto a wettable powder. The percent moisture in this extrudable paste was determined by weighing the jar containing the wettable powder before and after the water additions, and then dividing the weight of the added water by the weight of the extrudable wet mixture and multiplying by 100%. The granular bulk density was determined as the apparent density of loosely packed material. Specifically, 10 grams of material was poured into a 100 mL graduated cylinder and the volume was measured. The bulk density in pounds per cubic foot was calculated as 624 divided by this measured volume. The granules exhibited properties as summarized in the following tables.

TABLE 1

| DISPERSANT | PASTE (% $H_2O$) | GRANULE (bulk density; lbs/ft$^3$) | ATTRITION (% < 400 MICRONS) | |
|---|---|---|---|---|
| | | | t = 0 | t = 1 month @ 54° C. |
| LLS | 10.3 | 33.0 | 55 | 55 |
| APS + LLS(liq) | 11.5 | 40.3 | 0 | 0.1 |
| APS + LLS(dry) | 7.5 | 39.0 | 0.2 | 0.1 |
| HLS | 15.9 | 44.0 | 2 | 5 |
| APS + HLS(liq) | 14.6 | 48.0 | 0.5 | 0 |
| APS + HLS(dry) | 10.6 | 44.6 | 5 | 5 |
| MOREWET ® D-425 | 10.5 | 40.0 | 33 | 36 |
| KRAFTSPERSE ® EDF-350 | 12.5 | 37.0 | 28 | 12 |
| POLYFON ® F | 10.5 | 31.0 | 74 | 78 |

LLS = REAX ® 88B (a LS of lower MW)
HLS = REAX ® 85A (a LS of higher MW)
APS = AGRIMUL ® PG 2076
APS + LLS(liq) - APS and LLS were added to the WDG premix as a liquid blend
APS + LLS(dry) - APS and LLS were added to the WDG premix as a spray-dried solid
APS + HLS(liq) - APS and HLS were added to the WDG premix as a liquid blend
APS + LLS(dry) - APS and LLS were added to the WDG premix as a spray-dried solid

TABLE 2

| DISPERSANT | DISPERSIBILITY (342 PPM) | | SUSPENSIBILITY (342 PPM) | | SUSPENSIBILITY (1000 PPM) | |
|---|---|---|---|---|---|---|
| | t = 0 | t = 1 month @ 54° C. | t = 0 | t = 1 month @ 54° C. | t = 0 | t = 1 month @ 54° C. |
| LLS | 11 | 12 | 82 | 81 | 80 | 80 |
| APS + LLS(liq) | 11 | 12 | 84 | 83 | 83 | 81 |
| APS + LLS(dry) | 8 | 8 | 81 | 72 | 78 | 80 |
| HLS | 16 | 14 | 85 | 64 | 81 | 53 |
| APS + HLS(liq) | 13 | 15 | 84 | 83 | 81 | 85 |
| APS + HLS(dry) | 5 | 6 | 87 | 79 | 81 | 76 |
| MOREWET ® D-425 | 16 | 14 | 63 | 68 | 51 | 65 |
| KRAFTSPERSE ® EDF-350 | 7 | 8 | 80 | 78 | 79 | 76 |
| POLYFON ® F | 5 | 3 | 90 | 85 | 85 | 46 |

LLS = REAX ® 88 (a LS of lower MW)
HLS = REAX ® 85A (a LS of higher MW)
APS = AGRIMUL ® PG 2076
APS + LLS(liq) - APS and LLS were added to the WDG premix as a liquid blend
APS + LLS(dry) - APS and LLS were added to the WDG premix as a spray-dried solid
APS + HLS(liq) - APS and HLS were added to the WDG premix as a liquid blend
APS + LLS(dry) - APS and LLS were added to the WDG premix as a spray-dried solid

EXAMPLE 7

A series of extruded granules were made as in Example 6 except that the technical chlorothalonil was air-milled to a smaller particle size (median diameter=19 microns, compared with a median diameter of 28 microns for the compositions used in examples 4 and 5), and the amount of composite dispersant was varied, using sodium sulfate as the adjustable filler. As summarized in the following table, the dispersional stability was determined by measuring the suspensibility initially (t=0), meaning within 24 hours of drying the granules, and after one month (t=1) of accelerated aging at 54° C. Entries under "S" are weight percentages of SELLOGEN® W in the formulations and those marked "SS" are for weight percentages of anhydrous sodium sulfate.

| | S | SS | t = 0 | t = 1 |
|---|---|---|---|---|
| Disp (c) | | | | |
| 4% | 3 | 9 | 96 | 20 |
| 6% | 3 | 7 | 94 | 51 |
| 8% | 3 | 5 | 97 | 73 |
| 10% | 3 | 3 | 97 | 95 |
| 12% | 3 | 1 | 99 | 96 |
| 16% | 0 | 0 | 99 | 97 |
| Disp (d) | | | | |
| 4% | 3 | 9 | 96 | 30 |
| 6% | 3 | 7 | 96 | 66 |
| 8% | 3 | 5 | 97 | 93 |
| 10% | 3 | 3 | 98 | 94 |
| 12% | 3 | 1 | 99 | 94 |

Disp (C) is APS + LLS(dry)
Disp (d) is APS + HLS(dry)

EXAMPLE 8

A concentrated aqueous solution of sodium lignosulfonate (CAS 8061-51-6) sold by Westvaco under the tradename KRAFTSPERSE® EDF-750, a neutral pH dispersant/disintegrant based on a high degree of sulfonation, low molecular weight kraft lignin was blended with AGRIMUL® PG 2067 Surfactant. The pH of the solution was adjusted to about 7.0 by adding sulfuric acid. Then, this mixture was spray dried. After spray drying, the composite spray-dried dispersant contained (on a DRY weight basis) 85–90% sodium lignosulfonate and 10–15% alkyl polyglycoside. Thus, the alkyl polyglycoside to lignosulfonate ratio in this blend falls in the range from 1:9 ratio (10% alkyl polyglycoside) to a 15:85 ratio (15% alkyl polyglycoside).

EXAMPLE 9

The procedure of Example 3 was repeated wherein 11.1 Kg AGRIMUL® PG 2069 and 38.9 Kg REAX® 88B were used. However, this mixture was acidified to pH 4.5 by adding sulfuric acid. After spray drying, the composite spray-dried dispersant contained (on a DRY weight basis) about 75% sodium lignosulfonate and about 25% alkyl polyglycoside. The spray-dried solid was observed to flow freely and dissolved completely in water at 21° C.

What is claimed is:

1. A composite dispersing agent comprising an alkyl polyglycoside and a polymeric anionic dispersant.

2. The composite dispersing agent of claim 1 wherein the weight ratio of alkyl polyglycoside to the polymeric anionic dispersant is from about 1:9 to about 9:11.

3. The composite dispersing agent of claim 2 wherein the weight ratio of alkyl polyglycoside to polymeric anionic dispersant is about 1:4 to about 7:13.

4. The composite of claim 1 wherein the polymeric anionic dispersant is a sulfonated lignin.

5. The composite of claim 1 further comprising a nonionic, anionic, cationic or amphoteric surfactant or a combination thereof.

6. The composite of claim 5 wherein the anionic surfactant is a naphthalene sulfonate.

7. The composite of claim 1 wherein the alkyl polyglycoside is a compound of the formula I $$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6.

8. The composite of claim 7 wherein $R_1$ is an alkyl group having from about 8 to about 10 carbon atoms and a is a number equal to about 1.5.

9. A composite dispersing agent comprising an alkyl polyglycoside of the formula I $$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6 and a sulfonated lignin.

10. The composite of claim 9 wherein the weight ratio of alkyl polyglycoside to the sulfonated lignin is from about 1:9 to about 9:11.

11. The composite dispersing agent of claim 10 wherein the weight ratio of alkyl polyglycoside to the sulfonated lignin is about 1:4 to about 7:13.

12. The composite dispersing agent of claim 11 wherein the weight ratio of alkyl polyglycoside to the sulfonated lignin is about 1:3.

13. A composition comprising a pesticide and an effective amount of composite dispersing agent comprising an alkyl polyglycoside and a polymeric anionic dispersant.

14. The composition of claim 13 wherein the weight ratio of alkyl polyglycoside to the polymeric anionic dispersant is from about 1:9 to about 9:11.

15. The composition of claim 14 wherein the weight ratio of alkyl polyglycoside to polymeric anionic dispersant is about 1:4 to about 7:13.

16. The composition of claim 13 wherein the polymeric anionic dispersant is a sulfonated lignin.

17. The composition of claim 13 further comprising a nonionic, anionic, cationic or amphoteric surfactant or a combination thereof.

18. The composite of claim 5 wherein the anionic surfactant is a naphthalene sulfonate.

19. The composition of claim 13 wherein the alkyl polyglycoside is a compound of the formula I $$R_1(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6.

20. The composition of claim 19 wherein $R_1$ is an alkyl group having from about 8 to about 10 carbon atoms and a is a number equal to about 1.5.

* * * * *